United States Patent [19]

Sioli et al.

[11] 3,978,120

[45] *Aug. 31, 1976

[54] METHOD FOR THE PRODUCTION OF ALICYCLIC ANHYDRIDES

[75] Inventors: Giancarlo Sioli, Como; Luigi Giuffre, Milan; Franco Righi, Cesano Maderno; Giancarlo Matera, Milan, all of Italy

[73] Assignee: Sniz Viscosa Societa Nazionale Industria Applicazioni Viscosa S.p.A., Milan, Italy

[ * ] Notice: The portion of the term of this patent subsequent to Oct. 21, 1992, has been disclaimed.

[22] Filed: Feb. 18, 1975

[21] Appl. No.: 550,262

Related U.S. Application Data

[62] Division of Ser. No. 118,951, Feb. 25, 1971, Pat. No. 3,914,313.

[52] U.S. Cl. .............................. 260/547
[51] Int. Cl.² ............................ C07C 51/56
[58] Field of Search ....................... 260/547

[56] References Cited
UNITED STATES PATENTS

| | | | |
|---|---|---|---|
| 1,735,959 | 11/1929 | Dreyfus | 260/547 |
| 1,872,029 | 8/1932 | Dreyfus | 260/547 |
| 1,872,030 | 8/1932 | Dreyfus | 260/547 |
| 1,990,902 | 2/1935 | Green | 260/547 |
| 1,991,085 | 2/1935 | Dreyfus | 260/547 |
| 2,054,865 | 9/1936 | Opley et al. | 260/547 |
| 2,483,883 | 10/1949 | Corbiere et al. | 260/547 |
| 2,856,426 | 10/1958 | Estabrook | 260/547 |
| 2,872,481 | 2/1959 | Vogt | 260/547 |
| 3,378,583 | 4/1968 | Bogaert | 260/547 |

FOREIGN PATENTS OR APPLICATIONS

| | | | |
|---|---|---|---|
| 2,109,266 | 2/1970 | Germany | 260/547 |

*Primary Examiner*—Lewis Gotts
*Assistant Examiner*—D. R. Phillips
*Attorney, Agent, or Firm*—Shlesinger, Fitzsimmons & Shlesinger

[57] ABSTRACT

A method is disclosed for the preparation of alicyclic anhydrides, useful as intermediates in the preparation of alicyclic ketenes which can be converted into lactams. The instant method comprises heat-treating an alicyclic acid in a metallic reactor, free of nickel, under subatmospheric pressure. A catalyst, such as an alkyl ester of selenphosphoric acid, has given good results.

13 Claims, No Drawings

METHOD FOR THE PRODUCTION OF ALICYCLIC ANHYDRIDES

This application is a division of our application Ser. No. 118,951, filed Feb. 25, 1971, now U.S. Patent No. 3,914,313, issued Oct. 21, 1975.

This invention relates to a method for the preparation of alicyclic anhydrides, this term being intended to connote the compounds in which the carbonyl grouping is directly bound to a carbon atom of the cycloaliphatic ring, that is, compounds of the general formula:

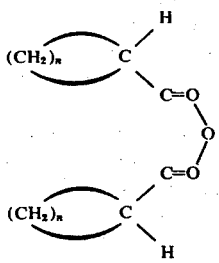

Such compounds can be used, for example, for the preparation of alicyclic ketenes which can be converted into lactams, these being industrially important compounds for the preparation of polymers adapted to be converted into fibers, plastics materials and the like, or other products having a wide range of industrial applications.

According to the invention, a method has been envisaged, whereby alicyclic anhydrides are prepared with good yields, the reaction times being short, and the operative conditions are the most suitable ones for an industrial use of the subject method.

According to the method of the present invention, an alicyclic acid, is subjected to a heat treatment in metallic reactors at high temperatures and under a reduced pressure, which permits the anhydride to be obtained with a high purity, with good yields and conversion ratios. More particularly, the subject method can be applied to the preparation of the anhydride of hexahydrobenzoic acid, a substance which has a great industrial importance, inasmuch as it can be converted into cyclopentamethyleneketene and this in turn into its corresponding lactam (epsilon-caprolactam) used in the production of polycaprolactam, or Nylon-6, from which fibers, plastics materials and the like are produced. The starting alicyclic acid is, in this case, hexahydrobenzoic acid.

However, the method according to the invention permits also that other anhydrides be prepared, which belong to the family of alicyclic or cycloalphatic anhydrides and, in general, the method and the reaction runs contemplated in it can be applied, as well, to the preparation of any alicyclic anhydride.

The method according to the invention is carried out in metallic reactors, generally copper vessels or vessels made of steel having a variable composition (such as steels containing chromium, manganese and other elements) which are capable of withstanding the action of reactants and of the formed products, but substantially devoid of nickel.

The subject method can be carried out with the aid of appropriate catalysts which accelerate the reactions, other substances being possibly added to improve the catalyst efficiency by overcoming possibly detrimental side effects.

According to the invention, the alicyclic acid is subjected to heat treatment within a metallic reactor at a temperature between 400°C and 900°C and preferably between 550°C and 750°C under reduced pressures, preferably less than 100 millimeters of mercury (mmHg), gases and vapors being produced which are subsequently separated by fractional condensation.

The metallic reactor to be employed is preferably made of copper or a special steel which contains chromium, manganese and other elements, but which is virtually devoid of nickel values.

The alicyclic acid used as the starting material is fed to a reactor which is maintained under the temperature and pressure conditions outlined above, but preferably under a residual pressure of less than 100 mmHg, and at a temperature from 550°C to 750°C, the presence of a phosphorus-containing catalyst being preferred. Generally phosphoric acid esters of the type $XP(OR)_3$ are used, wherein the substituent X indicates oxygen, sulphur, selenium, and R is an alkyl radical.

The amounts of such catalysts, which are used, as a rule, range from 0.1 percent to 2.5 percent by weight with respect to the starting acid used. The preferred amounts range between 0.3 percent and 1 percent.

According to a practicable embodiment of the method, it has been ascertained that the vapors emerging from the reactor can be supplemented, with advantage, by small amounts of ammonia or aliphatic or heterocyclic amines (such as pyridine) which prevent the occurrence of side reactions detrimental to the efficiency of the subject method. The amounts employed of these nitrogenous compounds range from 0.05 to 10 per thousand by weight with respect to the starting acid.

The vapors emerging from the reactor are fed to a set of condensers (generally two or three) which are kept at decreasing temperatures so as to obtain a fractional condensation of said vapors. As a rule, the first condenser is kept at such temperatures that the unreacted starting acid vapors and the anhydride of said acid are condensed.

The vapors formed during the reaction can go, at least partially, beyond the first condenser and be then properly cooled and separated. On the contrary, and frequently, the vapors react thoroughly, once they come out of the reactor, with a portion of the unreacted acid, thus producing the anhydride thereof, which is condensed together with the acid in the first condenser. In such case, the vapors emerging from the first condenser consist of the water formed in the main reaction and of by-products, and are fed to the second condenser (or to a sequential set of condensers) which is kept at temperatures lower than that of the first one, and generally at sub-zero temperatures, so that they are condensed and withdrawn. From the acid-anhydride mixture as collected in the first condenser, the anhydride can be separated with conventional distillation steps.

The conversion ratios as obtained are, as a rule, in the order of 60–80 percent, sometimes even higher (about 80–90 percent). The yields are generally very high, about 85–95 percent, and very often they approach the theoretical values. The purity of the anhydride thus obtained is extremely satisfactory and is in the order of 96–99 percent. The method of the invention can be carried out both as a batch process and as a continuous run according to the most updated techniques of this field.

According to what has been ascertained by the applicants, a novel catalyst consisting of alkyl esters of the selenophosphoric acid has given particularly satisfactory results. By using such a catalyst, very high yields and conversion ratios have been obtained, the conversion rates attaining even 80–90 percent.

In order that the invention may be further illustrated, a few examples of practical use will be described, these being in no wise intended as limitations of the modes of operation and the details used in carrying out the invention.

EXAMPLE 1

A 3-meter copper tube having a diameter of 8mms. is heated to a temperature of 640°–660°C and fed, under a pressure of 20 Torr. and at a rate of flow of 300 grms. an hour, with 912 grms. of hexahydrobenzoic acid (97.2% purity), supplemented with 1% of triethylselenophosphate as a catalyst. On completion of the reaction, the gases are caused to pass through a condenser kept at 60°C where 345.6 grms. of hexahydrobenzoic acid, and 483.26 grms. hexahydrobenzoic acid anhydride are collected along with small amounts of by-products. In subsequently placed traps, kept at temperatures lower than zero centigrade, 38 grms. of water are collected together with about 40 grms. of low-boiling by-products. The conversion ratio is 61% and the yield of the converted product is 96%. The thusly obtained anhydride is concentrated by distillation until an anhydride is obtained having a purity of 96.63% and 2% by weight of hexahydrobenzoic acid.

EXAMPLE 2

A tube made of special chromium-steel (free of nickel) having a diameter of 16 mms. and a length from 1 to 3 meters is heated to a temperature of 640°–660°C and fed, under a pressure of 20 Torr. and with a rate of flow of 300 grms. an hour, with 895 grms. of hexahydrobenzoic acid (97.2% purity) containing 0.5% by wt. of triethylselenophosphate. The emerging gases are cooled in a first condenser kept at 60°C and in sequentially arranged traps kept at subzero temperatures. 417.53 grms. hexahydrobenzoic acid, 378.10 grms. hexahydrobenzoic acid anhydride, 36 grms. water and the balance consisting of by-products are obtained. The yield of the reaction is 90%, the conversion ratio is 52%.

The anhydride thus obtained is concentrated up to 96.63% by distillation. This anhydride contains 2% of acid.

EXAMPLE 3

The reactor described in Example 1 is fed, under a pressure of 20 Torr. and at a rate of flow of 300 grams an hour, at a temperature of 700°C, with 930 grms. of hexahydrobenzoic acid (97.2% purity) supplemented by 1% of triethylselenophosphate. The outlet end of the reaction tube is fed with 0.1% of gaseous ammonia. On completion of this stage one obtains 114.62 grms. hexahydrobenzoic acid, 716.38 grms. anhydride, with a conversion ratio of 87% and a yield of 98%. The anhydride is purified and concentrated. It is obtained with a purity of 96.63% and contains 2% by wt. of hexahydrobenzoic acid.

EXAMPLE 4

A copper reactor similar to the one described in Example 1 is fed, at a rate of flow of 300 grms. an hour, at a temperature of 640°–660°C and under a pressure of 20 Torr., with 902 grms. of hexahydrobenzoic acid (98.84% purity) supplemented by 0.3% by weight of triethylthiophosphate. Downstream of the reactor, one collects 553.04 grms. acid, 287.23 grms. of anhydride, and a few grams of by-products, the conversion ratio being 38% and the yield 91%.

EXAMPLE 5

A reactor similar to the one of Example 1 is fed, at a rate of flow of 300 grms. an hour, at a temperature of 700°C and under a pressure of 20 Torr., with 883 grms. hexahydrobenzoic acid (98.84% purity) supplemented by 0.5% by wt. of triethylphosphate. One obtains 406.78 grms. acid, 369.79 grms. anhydride, 45 grms. water and a few by-products, the conversion rate being 53% and the yield of the converted product 85%.

The thusly obtained anhydride can then be converted into a ketene.

EXAMPLE 6

A tubular copper reactor similar to the one described in Example 1, heated to a temperature of 650°–670°C, is fed, under a pressure of about 20 Torr. and at a rate of flow of 400 g/h, with 1200 grs. of cyclododecancarboxylic acid (98.5% purity) kept molten by means of an oil-circulating jacket at a temperature of 110°C; the molten acid is supplemented by 0.2% by weight of triethylthiophosphate. At the reactor outlet the gases are supplemented by 1% of gaseous $NH_3$ and abruptly cooled to 120°C. The unreacted acid and its anhydride are thus recovered, while the ketene and water vapours are condensed at sub-zero temperatures. One obtains 390 grs. of acid, 30 grs. of anhydride, 610 grs. of cycloundecamethyleneketene and 90 grs. of $H_2O$, the conversion ratio being 67%.

EXAMPLE 7

A tubular copper reactor similar to the one described in Example 1, heated to a temperature of 650°C, is fed, under a pressure of 20 Torr. and at a rate of flow of 350 g/h, with 1000 grs. of cyclo-octancarboxylic acid (98% purity), kept molten by means of a water-circulating jacket at a temperature of 75°–80°C; the molten acid is supplemented by 0.25% by weight of triethylthiophosphate. At the reactor outlet the gases are supplemented by about 1% of gaseous ammonia and abruptly cooled to 100°C. The unreacted acid and its anhydride are thus recovered, while the ketene and water vapours are condensed at sub-zero temperatures. One obtains 245 grs. of acid, 35 grs. of anhydride, 575 grs. of cycloheptamethyleneketene and 70 grs. of $H_2O$ with a conversion of 75%.

Having thus described our invention, what is claimed is:

1. A method for the preparation of alicyclic anhydrides comprising heating an unsubstituted alicyclic acid, which is of the type represented by a carbonyl grouping directly bound to a carbon atom of cycloaliphatic ring, at a temperature between 550°C and 750°C, and under a pressure of less than 100 mm. Hg. in a metallic reaction vessel made of a metal other than nickel, and in the presence of a catalyst which is an ester of phosphoric acid of the type XP (OR)$_3$, where X is selected from the group consisting of oxygen, sulphur and selenium, and R is an alkyl radical, and fractionally condensing the gases and vapors obtained to recover the desired anhydride.

2. A method according to claim 1, wherein the alicyclic acid is subjected to heat treatment at a temperature between 600°C and 700°C, and the gases and vapors produced are fractionally condensed in a first condenser, producing a mixture of said acid and of alicyclic acid anhydride, and the anhydride is separated from the mixture.

3. A method according to claim 1, wherein the acid used is hexahydrobenzoic acid, and the product obtained is hexahydrobenzoic acid anhydride.

4. A method according to claim 1, wherein the acid used is cyclododecancarboxylic acid, and the product obtained is cyclododecancarboxylic acid anhydride.

5. A method according to claim 1, wherein the amount of catalyst used is between 0.1 percent and 2.5 percent by weight with respect to the amount of starting acid used.

6. A method according to claim 5, wherein the amount of catalyst used is between 0.3 percent and 1 percent of the starting acid used.

7. A method according to claim 2, wherein the gases and vapors emerging from the reaction vessel are supplemented by a nitrogenous compound selected from the group consisting of ammonia and pyridine in an amount between 0.05 and 10 per thousand by weight with respect to the starting acid.

8. A method according to claim 6, wherein the catalyst is an alkyl ester of selenophosphoric acid.

9. A method for producing an alicyclic anhydride for use in preparation of alicyclic ketenes comprising heating hexahydrobenzoic acid to a temperature between 630° and 700°C in a reactor, which is free of nickel, under a pressure of 20 Torr. in the presence of a catalyst selected from the group consisting of triethylselonophosphate, triethylthiosphate and triethylphosphate in an amount of 0.3% to 1% by weight, condensing the gases from the reactor at a temperature of 60°C to collect a mixture of hexahydrobenzoic acid and hexahydrobenzoic acid anhydride, separating the acid anhydride from the acid, and concentrating the anhydride until an anhydride having a purity of 96.63 and 2% by weight of hexahydrobenzoic acid is obtained.

10. A method according to claim 9, wherein the outlet end of the reactor is fed with gaseous ammonia in an amount of 0.05 to 10 per thousand by weight of the starting acid before condensing the mixture.

11. A method according to claim 2, wherein the mixture from the reactor is fed to a distillation column and the hexahydrobenzoic acid is collected from the top of the column and the anhydride is obtained at the tail of the column.

12. A method according to claim 1, wherein the starting acid is cyclododecancarboxylic acid and this is heated in the presence of 0.2% by weight of triethylthiophosphate as a catalyst, the reactor is tubular, 1% of ammonia is added to the gases at the outlet of the tubular reactor, the gases are then abruptly cooled to 120°C, and the unreacted acid and its anhydride are recovered.

13. A method according to claim 1, wherein the starting acid is cyclo-octancarboxylic acid, and this is heated in the presence of 0.25% by weight of triethylthiophosphate as a catalyst, the reactor is tubular, 1% of gaseous ammonia is added to the gases at the outlet end of the reactor and the gases are then abruptly cooled to 100°C, and the unreacted acid and its anhydride are recovered.

* * * * *